US00PP10633P

United States Patent [19]

Meilland

[11] Patent Number: Plant 10,633

[45] Date of Patent: Oct. 6, 1998

[54] HYBRID TEA ROSE PLANT NAMED 'MEINICAL'

[75] Inventor: Alain A. Meilland, Antibes, France

[73] Assignee: CP (Delaware) Inc., Wilmington, Del.

[21] Appl. No.: 834,866

[22] Filed: Apr. 10, 1997

[51] Int. Cl.[6] ..... A01H 5/00

[52] U.S. Cl. ..... Plt./21

[58] Field of Search ..... Plt./20, 21

[56] References Cited

PUBLICATIONS

UPOU–ROM, 1997/06, Plant Variety Database, GTI Jouve Retrieval Software, 3 citations for 'Meinical', 1997.

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which forms attractive long-lasting currant red blossoms that commonly open slowly and completely. The blossom coloration commonly is stable during the course of opening. The stems are strong and the thorns tend to be few in number. The plant exhibits dark green and glossy foliage, as well as good disease resistance. The new variety is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Meitulandi' variety (non-patented in the United States). The male parent (i.e., the pollen parent) was the 'Jelvanica' variety (non-patented in the United States). The parentage of the new variety can be summarized as follows:

'Meitulandi'×'Jelvanica'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive long-lasting Current Red blossoms that commonly open slowly and completely,
(b) exhibits an erect growth habit with strong stems and few thorns,
(c) forms attractive dark green and glossy foliage,
(d) exhibits good disease resistance, and
(e) is particularly well suited for cut flower production when grown under greenhouse conditions.

When the new variety of the present invention is compared to the parent 'Meitulandi' variety, it is found that the new variety unlike such parent exhibits no fragrance, possesses slightly truncated petals, and more rigid and greener foliage. When the new variety of the present invention is compared to parent 'Jelvanica' variety, it is found that the new variety exhibits larger blossoms of a darker red coloration, foliage that is greener and more brilliant, and thicker stems.

The new variety well meets the needs of the horticultural industry during the commercial production of cut flowers. The blossoms commonly display a deep velvet red appearance in the absence of burning. Good color stability is manifest by the blossoms during the course of opening. Such color stability commonly is observed on the plant and when the blossoms are cut and present in a vase.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meinical' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud at the opening of the sepals;

FIG. 3—illustrates a specimen of a floral bud at the opening of the petals;

FIG. 4—illustrates a specimen of a flower in the course of opening;

FIG. 5—illustrates a specimen of an open flower—plan view—obverse;

FIG. 6—illustrates a specimen of an open flower—plan view—reverse;

FIG. 7—illustrates a specimen of a fully open flower—plan view—obverse;

FIG. 8—illustrates a specimen of a fully open flower—plan view—reverse;

FIG. 9—illustrates a specimen of a floral receptacle showing the arrangement of the stamens and pistils;

FIG. 10—illustrates a specimen of a floral receptacle showing the arrangement of the pistils (stamens removed);

FIG. 11—illustrates a specimen of a flowering stem;

FIG. 12—illustrates a specimen of a main branch;

FIG. 13—illustrates a specimen of a leaf with three leaflets—plan view—upper surface;

FIG. 14—illustrates a specimen of a leaf with five leaflets—plan view—under surface; and FIG. 15—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year-old plants during November while budded on *Rosa indica* understock and growing in greenhouses at Le Cannet des Maures, Var, France. The coloration in common terms precedes reference to the chart in some instances.

Class: Hybrid Tea.

Plant:

*Height*.—When the plant is pruned to a height of 85 cm., floral stems having a length of approximately 40 to 60 cm. are commonly produced.

*Habit*.—Erect.

Branches:

*Color*.—Young stems: Green Group 137B, and more or less toned with reddish-brown coloration. Adult wood: Green Group 137B.

*Thorns*.—Size: small. Color: near Yellow Group 5C. Quantity: few.

Leaves:

*Stipules*.—Adnate and pectinate.

*Petioles*.—Upper surface: dark green (near Yellow-Green Group 148A) and more or less Glandular. Under surface: dark green, and bear some small thorns.

*Leaflets*.—Number: 3,5 (most often), and 7. Shape: oval. Serration: single and regular (as illustrated). Texture: consistent. General appearance: dense, dark green, and glossy. Color (young foliage): Upper surface: Green Group 137A, and tinted with reddish coloration. Under surface: Green Group 137C. Color (adult foliage): Upper surface: dark green, Green Group 139A. Under surface: Green Group 137B.

Inflorescence

*Number of flowers*.—Usually one flower per stem with the opening commonly being slow and complete.

*Peduncle*.—Medium green in coloration (near Green Group 143A), smooth and the length is approximately 8 to 10 cm. on average.

*Sepals*.—Upper surface: tomentose, and greenish in coloration. (near Green Group 143A). Under surface: commonly include extensions, and near green Group 143A in coloration.

*Buds*.—Shape: conical and elongated. Length: approximately 3.5 cm. on average. Color upon opening: Upper surface: dark and velvet Currant Red, Red Group 46A. Under surface: Currant Red, Red Group 46A.

*Flower*.—Shape: cupped-elongated with a high center. Diameter: approximately 10 to 12 cm. on average. Color (when opening begins): Upper surface: dark and velvet Currant Red, Red Group 46A. Under surface: Currant Red, Red Group 46A. Color (when blooming): Upper surface: Currant Red, Red Group 46A. Under surface: Cardinal Red, Red Group 53B. Color (at end of opening): Upper surface: Currant Red, Red Group 46A. Under surface: Cardinal Red, Red Group 53B. Fragrance: none, is lacking. Lasting quality: approximately 12 14 days on the plant, and approximately 8 to 12 days when cut and placed in a vase with good color stability being displayed during opening. Petal number: double (as illustrated). Commonly approximately 20 petals per bloom on average plus approximately 2 or 3 petaloids. Petal shape: the base is cordiform and the edges are reflexed. Petal drop: the petals commonly detaching cleanly. Stamen number: approximately 97 on average. Anthers: ochre in coloration. Filaments: yellowish with fuchsia tip. Pistils: approximately 93 on average. Stigmas: strawlike in coloration. Styles: dark fuchsia in coloration, with a tomentose tip. Receptacle: light green, smooth, and in longitudinal section in the shape of a pitcher.

Development:

*Vegetation*.—Strong.

*Blooming*.—Commonly approximately 130 to 170 stems/m.$^2$ per year.

*Resistance to diseases*.—Excellent.

I claim:

1. A new and distinct variety of Hybrid Tea rose plant characterized by the following combination of characteristics:

(a) forms attractive long-lasting currant red blossoms that commonly open slowly and completely,
(b) exhibits an erect growth habit with strong stems and few thorns,
(c) forms attractive dark green and glossy foliage,
(d) exhibits good disease resistance, and
(e) is particularly well suited for cut flower production when grown under greenhouse conditions;

substantially as herein shown and described.

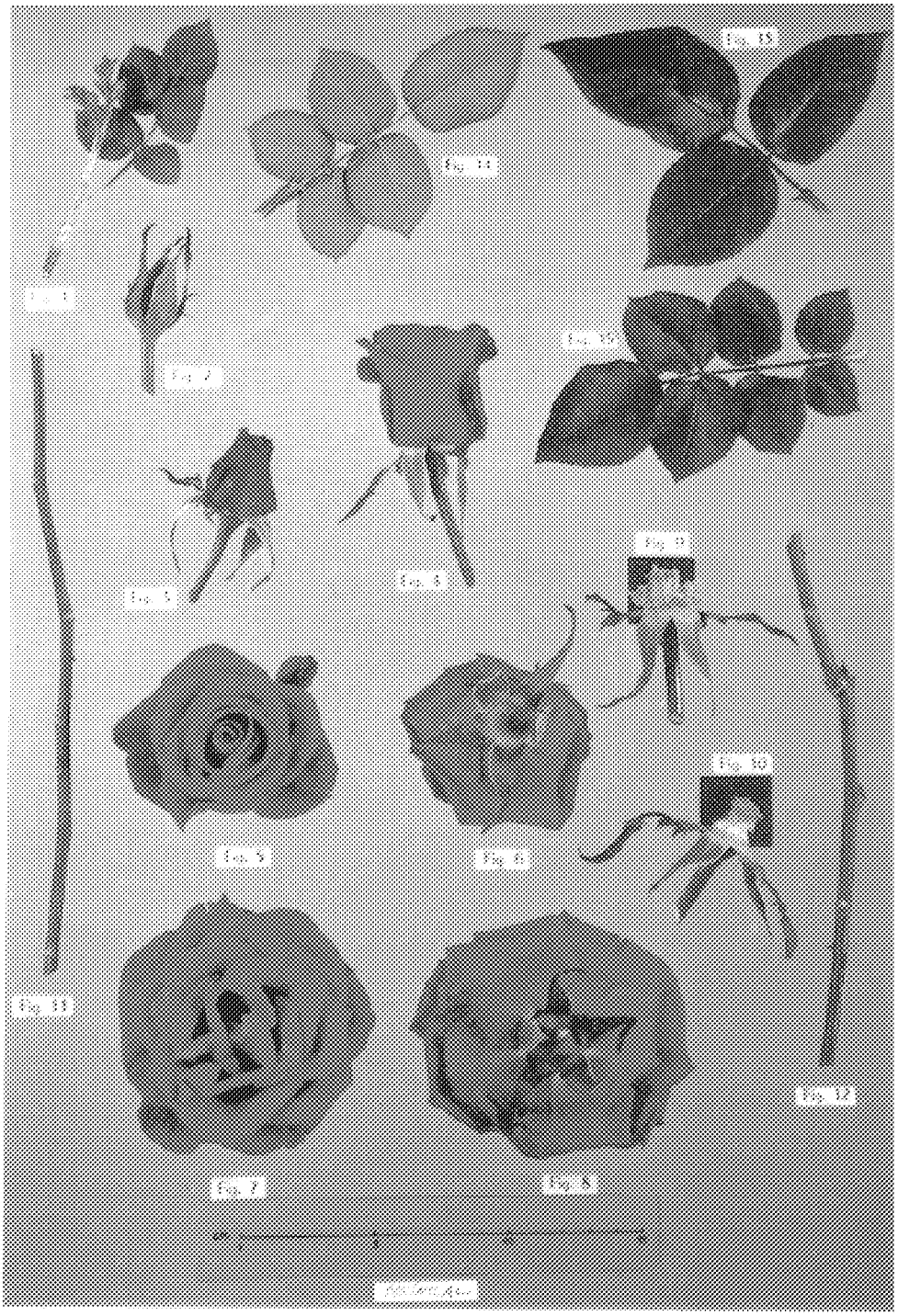

* * * * *